US009955864B2

(12) United States Patent
Rousseau et al.

(10) Patent No.: US 9,955,864 B2
(45) Date of Patent: May 1, 2018

(54) DEVICE AND METHOD FOR MEASURING SUBJECTIVE REFRACTION

(71) Applicant: ESSILOR INTERNATIONAL (COMPAGNIE GENERALE D'OPTIQUE), Charenton-le-Pont (FR)

(72) Inventors: Benjamin Rousseau, Charenton-le-Pont (FR); Martha Hernandez, Charenton-le-Pont (FR); Konogan Baranton, Charenton-le-Pont (FR); Pedro Ourives, Charenton-le-Pont (FR); Gildas Marin, Charenton-le-Pont (FR)

(73) Assignee: ESSILOR INTERNATIONAL (COMPAGNIE GENERALE D'OPTIQUE), Charenton-le-pont (FR)

( * ) Notice: Subject to any disclaimer, the term of this patent is extended or adjusted under 35 U.S.C. 154(b) by 0 days. days.

(21) Appl. No.: 15/105,932

(22) PCT Filed: Dec. 15, 2014

(86) PCT No.: PCT/FR2014/053335
§ 371 (c)(1),
(2) Date: Jun. 17, 2016

(87) PCT Pub. No.: WO2015/092244
PCT Pub. Date: Jun. 25, 2015

(65) Prior Publication Data
US 2016/0309999 A1 Oct. 27, 2016

(30) Foreign Application Priority Data
Dec. 17, 2013 (FR) ..................................... 13 62834

(51) Int. Cl.
*A61B 3/02* (2006.01)
*A61B 3/028* (2006.01)
(Continued)

(52) U.S. Cl.
CPC .......... *A61B 3/0285* (2013.01); *A61B 3/0008* (2013.01); *A61B 3/0025* (2013.01);
(Continued)

(58) Field of Classification Search
CPC .................................. A61B 3/103; A61B 3/02
(Continued)

(56) References Cited

U.S. PATENT DOCUMENTS

| 2,635,502 A | 4/1953 | Richards ........................ 351/202 |
| 5,104,214 A | 4/1992 | Sims ............................. 351/235 |

(Continued)

FOREIGN PATENT DOCUMENTS

| CN | 1842292 B | 2/2013 |
| DE | 4117754 | 12/1992 |

(Continued)

OTHER PUBLICATIONS

International Search Report and Written Opinion issued in PCT/FR2014/053335, dated Mar. 10, 2015.

*Primary Examiner* — Hung Dang
(74) *Attorney, Agent, or Firm* — Norton Rose Fulbright US LLP

(57) ABSTRACT

The invention relates to a device for measuring the subjective refraction of a person in near and/or medium vision, which comprises, according to the invention, for each eye of the person, a correction mounting (3) provided with at least one corrective lens, the correction mountings (3) being arranged such that the person looks through the lenses. The position of each correction mounting (3) is variable such as to adjust an angle (a) between the axes of the lenses.

19 Claims, 4 Drawing Sheets

(51) Int. Cl.
 *A61B 3/00* (2006.01)
 *A61B 3/032* (2006.01)
 *A61B 3/103* (2006.01)
 *A61B 3/04* (2006.01)
 *A61B 3/113* (2006.01)
 *A61B 3/14* (2006.01)

(52) U.S. Cl.
 CPC ............ *A61B 3/0091* (2013.01); *A61B 3/032* (2013.01); *A61B 3/04* (2013.01); *A61B 3/1035* (2013.01); *A61B 3/113* (2013.01); *A61B 3/14* (2013.01)

(58) Field of Classification Search
 USPC .......................... 351/235, 246, 234, 233, 222
 See application file for complete search history.

(56) References Cited

U.S. PATENT DOCUMENTS

| | | | | |
|---|---|---|---|---|
| 5,220,362 A | * | 6/1993 | Blenkle | A61B 3/0285 351/235 |
| 2004/0119944 A1 | | 6/2004 | Hosoi | 351/221 |

FOREIGN PATENT DOCUMENTS

| | | |
|---|---|---|
| FR | 2450096 | 9/1980 |
| WO | WO 2013/123044 | 8/2013 |

\* cited by examiner

DEVICE AND METHOD FOR MEASURING SUBJECTIVE REFRACTION

CROSS-REFERENCE TO RELATED APPLICATIONS

This application is a national phase application under 35 U.S.C. § 371 of International Application No. PCT/FR2014/053335 filed 15 Dec. 2013, which claims priority to French Patent Application No. 1362834 filed 17 Dec. 2014. The entire contents of each of the above-referenced disclosures is specifically incorporated by reference herein without disclaimer.

The invention relates to a device for measuring near- or intermediate-vision subjective refraction. The context of the invention is that of the measurement of parameters to be indicated on an optical prescription for a person requiring corrective eyewear, so as to correct visual defects such as myopia, hypermetropia, astigmatism and/or presbyopia. The invention also relates to a method for measuring near- and/or intermediate-vision subjective refraction.

Generally, and in the context of this description, near-vision is associated with distances of up to 70 cm, and intermediate-vision with distances of about 70 cm to four meters. Near vision may, for example, be associated with reading a book or a smart phone held in the hands, and intermediate vision with looking at a computer screen, a television screen or a dashboard of an automobile or with household tasks.

Devices and methods for measuring the subjective refraction of a person are known. A phoropter is especially used to determine the type (sphere and/or cylinder) and the power (measured in dioptres) of the required corrective eyeglasses. This phoropter forms part of an assembly called a refraction unit. A phoropter is a device having in its interior an eyeglass holder (or corrective holder) consisting of two holes and able to accommodate corrective eyeglasses. The phoropter has translational degrees of freedom in order to allow the corrective eyeglasses to be correctly positioned in front of the eyes of the person. To measure far-vision refraction, the person looks straight-ahead through the holes at an eye chart placed at infinity (for example, on a wall at about 5 to 6 m). Next, to measure near vision, the patient looks, through the phoropter, at a vertical reading plane, for example displaying a pattern, placed at a fixed distance of about 40 cm. For these measurements, the direction of the gaze of the person does not change relative to his head. The professional places corrective eyeglasses of various types and powers in the eyeglass holder and performs adjustments (for example, in order to adjust interpupillary distance), in order to determine the corrective eyeglass or the combination of eyeglasses offering the best possible vision, on the basis of the subjective feedback from the patient. Typically, to determine the optical prescription for near vision, an additional correction (consisting of at least one corrective eyeglass) is added to at least one corrective eyeglass corresponding to the prescription for far vision.

However, the technique described above does not take into account the convergence of the lines of gaze of the person in near vision. Specifically, when the person is looking at a near-vision reading plane, his gaze is convergent, the term "convergence" meaning that his eyes are turned so that their axes cross on the reading plane. In intermediate vision, the gaze is also convergent but to a lesser extent. In both cases, the gaze may also be lowered. Therefore, during the measurement of near and/or intermediate vision with the known method and devices, the axis along which the person looks is liable not to be well centered on the corrective eyeglasses, this possibly engendering aberrations and thus corrupting the values of the optical prescription. It is then possible for the spectacles prescribed to the person not to be optimally suited to the vision of the person. Furthermore, the technique described does not measure the modification to cylinder that the lowering of the gaze may cause.

The objective of the present invention is to remedy the aforementioned drawbacks by providing a device for measuring the near- and/or intermediate-vision subjective refraction of a person taking into account the convergence of the gaze of the person, in order to allow him to adopt a natural posture during the measurement and to allow optical aberrations to be minimized or prevented. The invention also provides a method for measuring the near- and/or intermediate-vision subjective refraction of a person.

According to a first aspect, the present invention relates to a device for measuring the near- and/or intermediate-vision subjective refraction of a person, the device comprising, for each eye of the person, a corrective holder equipped with at least one corrective lens, the corrective holders being arranged so that the person looks through the lenses.

The main feature of the device according to the invention is that the position of each corrective holder may be varied to adjust an angle between the axes of the lenses.

Such a device allows near- and/or intermediate-vision subjective refraction to be measured for a person in a natural position, the axes of the eyes being convergent, by virtue of the adaptability of the angle between the axes of the lenses and thus of the angle between the planes of the corrective holders, namely the planes of the lenses. The optical prescription determined or confirmed using the device according to the invention then allows a piece of corrective eyewear that is perfectly suited to the vision of the person, and especially his near and intermediate vision, to be designed. In addition, the adjustments of the corrective holder allow the device to be perfectly adapted to the morphology of the person.

Advantageously, the device furthermore comprises means for determining the direction of the gaze, so as to adjust the relative positions of the corrective holders in order to make the directions of the gaze of the two eyes converge with an angle of convergence, so as to guide the gaze of the person onto a pattern.

Preferably, the angle between the axes of the lenses is adjustable between 0° and 30°. This makes it possible to take account of various interpupillary distances and various distances between the eyes and the pattern. The angle between the planes of the corrective holders, which corresponds to the angle of convergence, may therefore vary, preferably, between 150° and 180°.

Preferably, the inclination of each corrective holder is regulatable. Thus, the directions of the gaze may be lowered by a pantoscopic angle.

Advantageously, the device according to the invention furthermore comprises a reading support arranged at a distance and angle that may be varied relative to the corrective holders, the reading support being intended to display the pattern.

According to one advantageous embodiment, the means for determining the direction of the gaze comprise, for each eye, a sight intended to be placed in front of the eye by means of the corrective holder.

Preferably, the sight includes an entrance element and an exit element able to be aligned along the direction of the gaze between the eye and the target.

For example, the sight may comprise a cylinder having an opaque or frosted cylindrical surface. The entrance and exit faces of the cylinder may, for example, comprise a sighting hole or a reticle.

According to another advantageous embodiment, the means for determining the direction of the gaze comprise means for acquiring and processing images. Preferably, the means for determining the direction of the gaze also comprise a light-emitting means emitting in the direction of the eyes of the person.

Preferably, the device according to the invention furthermore comprises adjusting means for decreasing the deviation between the position of the corrective holders and a setpoint position of the corrective holders, the positions being relative to the pattern, wherein the setpoint position corresponds to a position of the corrective holders in which the person looks perpendicularly through the center of the lenses.

Advantageously, the device according to the present invention comprises a means for discriminating the two eyes. Thus, it is possible to measure subjective refraction for each eye independently.

According to a second aspect, the present invention also relates to a method for measuring the near- and/or intermediate-vision subjective refraction of a person, by means of a device according to the invention, the method comprising a step of placing, in front of each eye of the person, by means of the corrective holder, at least one corrective lens corresponding to his near- and/or intermediate-vision prescription.

The main features of the method according to the invention are the following steps:
  varying the positions of the corrective holders in order to adjust an angle between the axes of the lenses; and
  determining the near- and/or intermediate-vision visual acuity of the person.

Particularly advantageously, the method according to the invention furthermore comprises the following steps:
  determining the direction of the gaze of the two eyes; and
  adjusting the relative positions of the corrective holders in order to make the directions of the gaze converge with an angle of convergence, so as to guide the gaze of the person onto the pattern.

According to a first advantageous embodiment, the step of determining the direction of the gaze comprises a step of placing, in front of each eye, by means of the corrective holder, the sight.

According to a second advantageous embodiment, the step of determining the direction of the gaze comprises a step of determining eye rotation center.

According to a third advantageous embodiment, the step of determining the direction of the gaze comprises a step of determining positions of the pupils.

Advantageously, the method furthermore comprises a step of inclining a plane containing the corrective holders in order to lower the directions of the gaze by a pantoscopic angle.

Advantageously, the step of measuring near- and/or intermediate-vision visual acuity comprises the following steps:
  placing means for discriminating the two eyes; and
  measuring the near- and/or intermediate-vision visual acuity for each eye independently.

Preferably, the method according to the invention furthermore comprises a step of iteratively adjusting, by means of adjusting means, the position of the corrective holders in order to decrease the deviation between the position of the corrective holders and a setpoint position of the corrective holders, the positions being relative to the pattern, wherein the setpoint position corresponds to a position of the corrective holders in which the person looks perpendicularly through the center of the lenses.

The invention and its advantages will be better understood with a view to the following description of embodiments of the invention, which embodiments are given by way of example and with reference to the appended figures, in which.

Figure 2A:
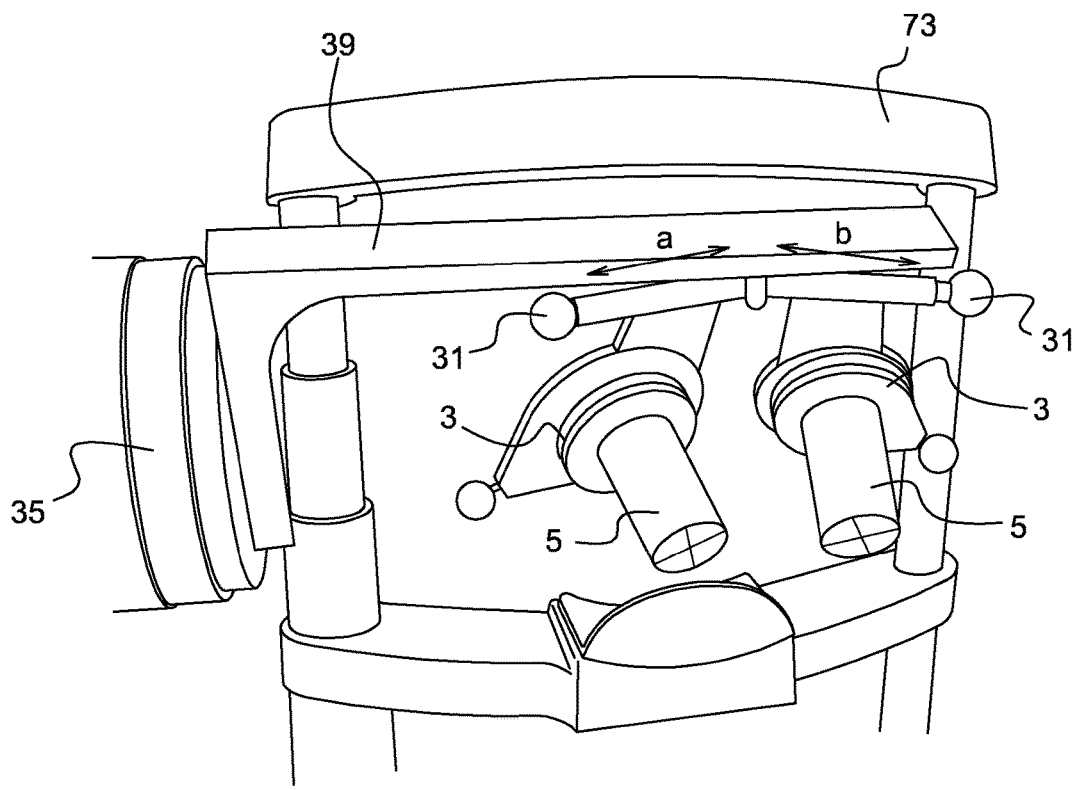
FIG. 2A shows, by way of example, a headrest and corrective holders equipped with sighting cylinders according to one embodiment of the invention.
Figure 2B:
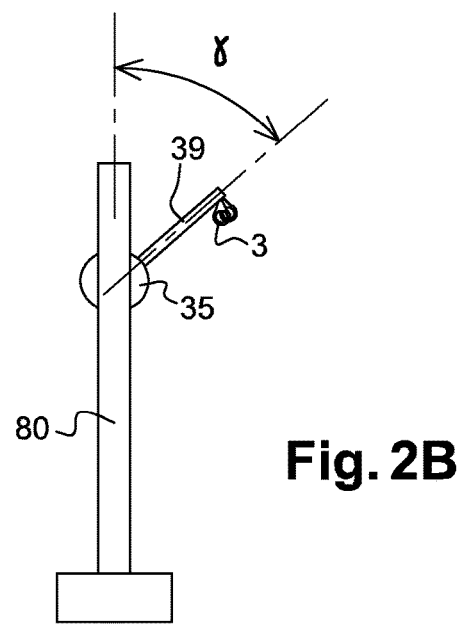
Figure 3A:
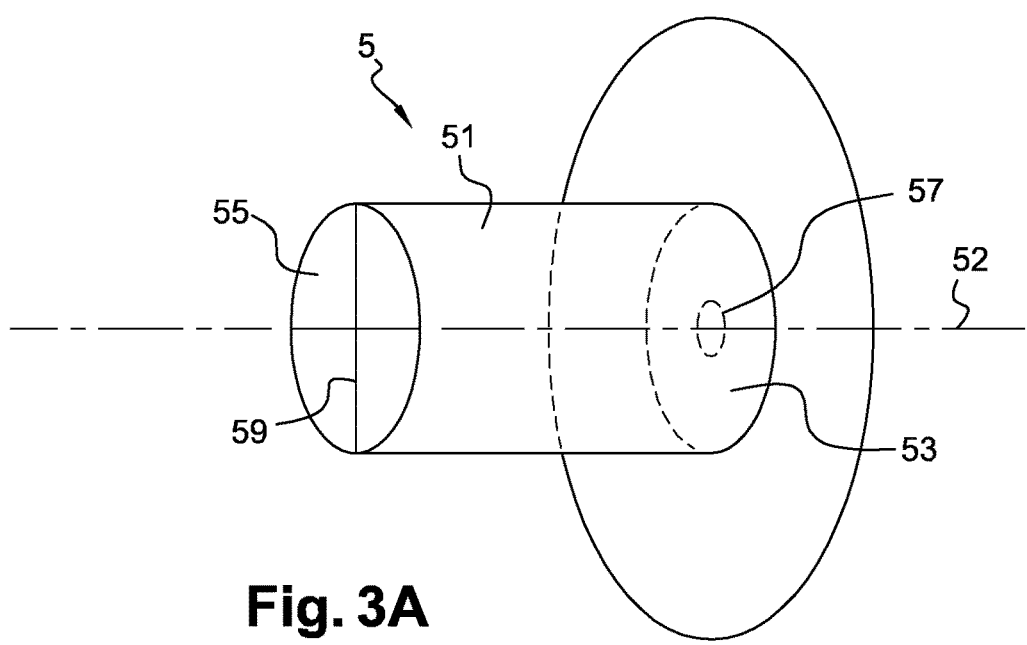
Figure 3B:
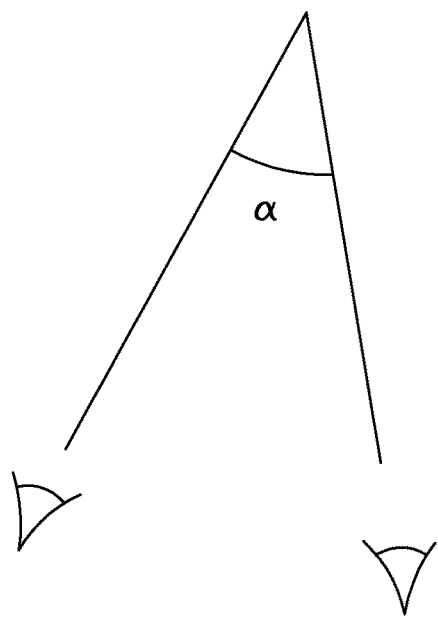
Figure 4A:
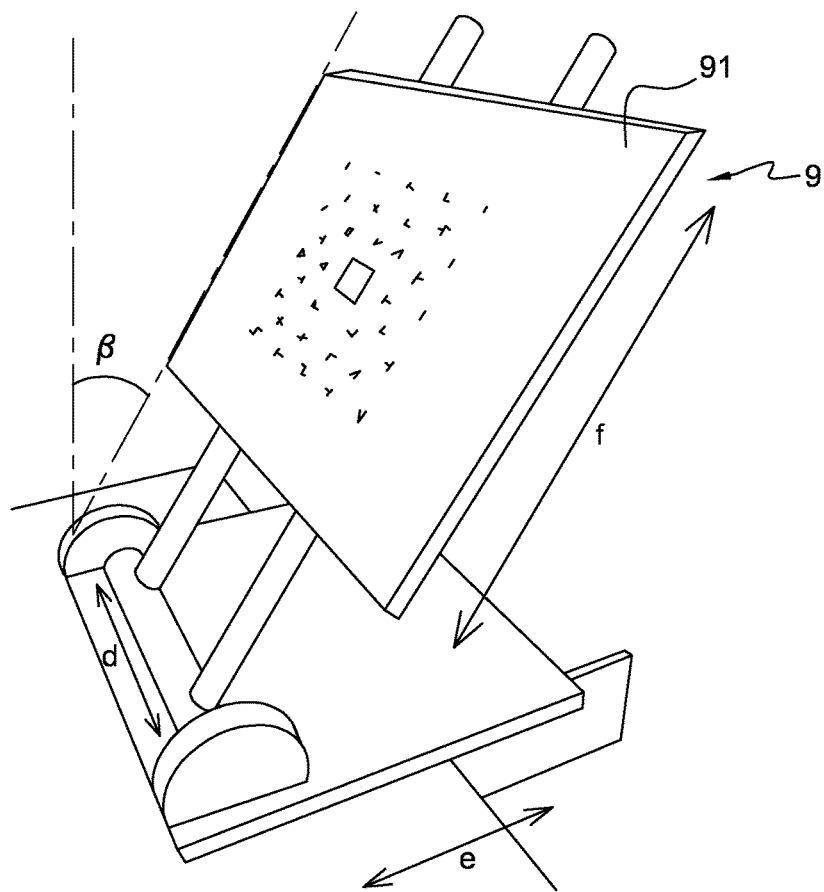
Figure 4B:
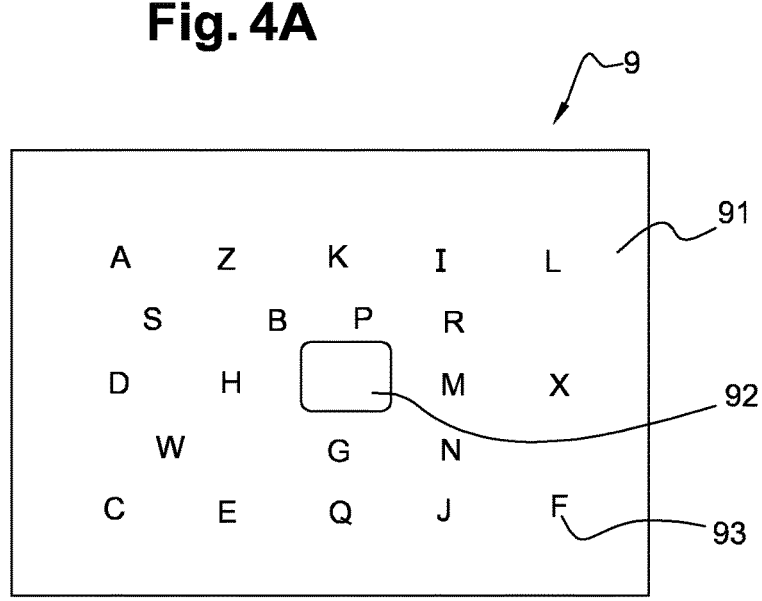

FIG. 2B schematically illustrates a side view of corrective holders having an angle of inclination to the vertical, according to one embodiment;

FIG. 3A schematically shows a sighting cylinder according to one embodiment of the invention;

FIG. 3B illustrates the angle of convergence between axes of the sighting cylinders;

FIG. 4A shows a view of a reading support of the device according to one embodiment; and FIG. 4B shows, by way of example, a front view of the reading support.

Figure 1:
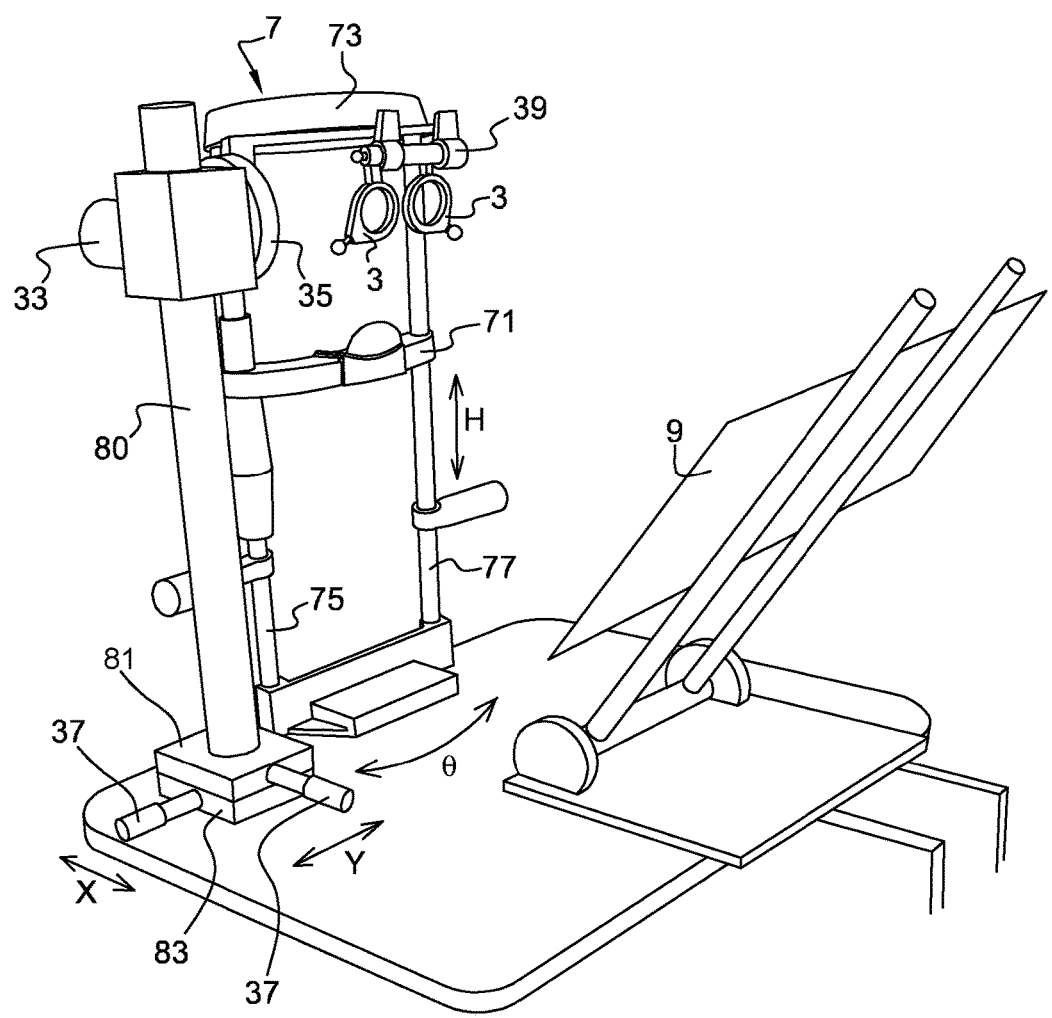
FIG. 1 shows a portion of a device for measuring the near- and/or intermediate-vision subjective refraction of a person according to one embodiment of the invention.

According to a first aspect, the present invention provides a device for measuring the near- and/or intermediate-vision subjective refraction of a person or patient. FIG. 1 shows a portion of a device for measuring the near- and/or intermediate-vision subjective refraction of a person according to one embodiment of the invention.

The device comprises, for each eye of the person, a corrective holder 3 intended to receive at least one corrective lens (not shown). The corrective holders 3 are arranged so that the person looks through the corrective lens for each eye. The corrective holders 3 may, for example, be of the type of a trial frame. A more detailed view of the corrective holders 3 is shown in FIG. 2A.

With reference to FIG. 2A, the device according to the embodiment shown furthermore comprises, for each eye of the person, a sight 5 defined by an axis and intended to be placed in front of the eye by means of the corrective holder 3. The relative positions of the corrective holders 3 are regulatable in order to make the axes of the sights converge, so as to guide the gaze of the person onto a pattern (not shown) allowing near- and/or intermediate-vision visual acuity to be measured. By "visual acuity", what is meant is visual performance in the broad sense, for example: actual visual acuity, sensitivity to contrast, sensitivity to haze and/or subjective appreciation of image quality. By "relative positions", what is meant is the relative position of one of the corrective holders 3 with respect to the other. For example, in FIG. 2A, the two corrective holders 3 are tipped one with respect to the other. The relative positions allow the angle of convergence $\alpha$ between the axes of the sights 5 to be defined (see also FIG. 3B). Thus for an angle of convergence $\alpha$ of zero, the corrective holders 3 are located in the same plane. The angle of convergence $\alpha$ varies as a function of the pupillary distance (IPD) of the person the subjective refraction of which is being measured, and of a sighting distance (D) between the corrective holders 3 and the pattern, and may be expressed as follows: $\alpha = \arctan(IPD/D)$. By way of example, for a sighting distance of 40 cm and a pupillary distance of 64 mm, the angle of convergence $\alpha$ is about 9.1°; for a sighting distance of 5 m and a pupillary distance of 64 mm, the angle of convergence $\alpha$ is about 0.7°. Preferably, the angle of convergence α and therefore the angle between the corrective holders 3 is adjustable between 0° and 30°.

The pattern may consist of characters such as letters, known optotypes such as a Landolt ring or by any other figure allowing visual acuity to be measured. The pattern may also be a duochrome test, for example a black letter on a red or green background. It may also be a test for measuring sensitivity to contrast, phoria, disparities and/or binocular vision.

The sights 5 may consist for example of cylinders 5, as shown in FIG. 2A. FIG. 3A schematically illustrates in more detail a cylindrical sight 5 according to one preferred embodiment. The cylinder 5 is hollow. It has a main axis 52, an opaque or frosted lateral cylindrical surface 51, a circular entrance face 53 that is placed near the eye and a circular exit face 55. The entrance face 53 consists of a disc having a larger diameter than the cylinder 5, which allows the cylinder 5 to be held in the corrective holder 3 (see FIG. 2A). The disc may be frosted or opaque. According to the embodiment illustrated in FIG. 3A, the entrance face 53 comprises a sighting hole 57 in order to guide the gaze in the cylinder 5. The sighting hole 57 has a stenopaic effect that increases depth of field. The exit face 55 comprises a cross-shaped reticle 59 for guiding the gaze onto the pattern. Alternatively, the entrance face 53 may also comprise, instead of the sighting hole, a reticle. By way of example, the length of the cylinder 5 is about 3 cm, its diameter is about 1 cm and the diameter of the hole 57 is about 2 mm.

The sight 5 allows the gaze to be limited to the axis of the sight 5. In practice, the positions of the corrective holders 3 are adjusted using sights 5 installed in the corrective holders 3. Thus, the axes of the gaze of the person are well determined and will be coincident with the optical axes of the corrective lenses. Next, the one or more corrective lenses are inserted into the corrective holders 3. Thus, the positions of the corrective holders 3 are adjusted so that the corrective lens or lenses are placed in the corrective holders 3 with their axes coincident with that of each eye. The patient therefore looks straight through the center of the corrective eyeglass (es). The optical prescription determined or confirmed using the device according to the invention then allows a piece of corrective eyewear that is perfectly suited to the vision of the person, and especially his near and intermediate vision, to be designed.

Particularly advantageously, the positions of the corrective holders 3 may therefore be adjusted in order to make, for each eye, the axis of the eye and the axis 52 of the sight 5 coincide. The one or more corrective eyeglasses intended to be placed in the corrective holders 3 are therefore also perfectly centered relative to the eyes of the patient.

With reference to the embodiment shown in FIG. 1, the device for measuring subjective refraction also comprises a headrest 7 so that the patient is able to rest his head behind the corrective holders 3. Typically, the headrest 7 consists of a chin rest 71 and a structure 73 against which the forehead may rest, the two structures 71, 73 being connected by a first fixed pole 75 and a second fixed pole 77. The poles 75, 77 are fastened to a table. It is also possible to fasten the poles 75, 77 to a stage (not shown) so as to allow the chin rest 71 and the structure 73 for resting the forehead to pivot about the vertical axis by an angle θ. It is also possible to incline the headrest structure 7 about a horizontal axis (not shown) so as to incline the head forward, the angle of inclination possibly, for example, being 20°. The structures 71, 73 for resting the chin and forehead are able to slide over the first and second poles 75, 77, in order to allow their height to be adapted to the morphology of the patient. As illustrated in FIGS. 1 and 2A, the corrective holders 3 may be installed using a movable arm 39 pivotably on a third pole 80 independent of the headrest 7. The corrective holders 3 may pivot conjointly about a horizontal axis, in order to be inclined at an angle of inclination γ to the vertical (see FIG. 2B), independently of the position of the headrest 7. This allows the corrective holders 3 to be correctly placed facing the eyes of the person, so that the axes of his eyes (or of his gaze) coincide with the axes of the sights 5, whatever the relative orientations of the head and eyes of the person. The angle γ is also called the pantoscopic angle of the corrective holders 3.

With reference to FIG. 1, the device for measuring subjective refraction furthermore comprises a reading support 9 arranged at a distance and angle that may be varied relative to the corrective holders 3. The reading support 9 is suitable for displaying the pattern.

Advantageously, the device for measuring subjective refraction comprises adjusting means for decreasing the deviation between the position of the corrective holders 3 and a setpoint position of the corrective holders 3, the positions being relative to the pattern. The term "position" must be understood to mean both the distance and the angle of inclination (pantoscopic angle) γ of the corrective holders 3 relative to the pattern and the reading support 9 that displays it. The setpoint position corresponds to a position, (in terms of distance and angle) relative to the pattern, in which the person looks perpendicularly through the corrective eyeglasses placed in the corrective holders 3 in order to see the pattern clearly.

More precisely and with reference to FIGS. 1 and 2A, the corrective holders 3 are provided with adjusting means 31 for adapting their distance to the pupillary distance of the person (arrows a and b), means 33 for adjusting height (arrow h) and means (not shown) for adjusting the angle of convergence α between the axes of the sights 5. The corrective holders 3 furthermore comprise adjusting means 35 for adjusting the inclination γ of the corrective holders 3 to the horizontal, and means 37 for applying a translational adjustment in the two horizontal directions (arrows x and y). The means 37 for applying a translational adjustment may consist of two translational stages 81, 83 able to translate the third pole 80 bearing the corrective holders 3. The reading support 9 is also provided with adjusting means, as detailed below.

FIGS. 4A and 4B show different views of the reading support 9 of the device according to one preferred embodiment of the invention. The reading support 9 comprises a board 91 on which is arranged a displaying means 92 able to display the pattern. The displaying means 92 may be an electronic displaying means, for example a liquid-crystal screen, or any other type of flatscreen. The size of the displaying means is preferably at least about 2 mm×2 mm to 20 mm×20 mm for the near-vision central portion. A display of 20 cm×20 cm will allow a peripheral portion to be included and will be more appropriate for larger intermediate-vision distances. The advantage of an electronic displaying means is that the type, size and other properties of the displayed pattern may be varied or adapted in real-time depending on how the device for measuring subjective refraction according to the invention is used. By way of example, for a sighting distance of 40 cm, the displayed pattern, such as a letter, may be <1 mm and, for example, 0.8 mm in size.

Around the displaying means 92 are arranged graphical signs or characters 93 (such as letters or numbers). The graphical signs 93 may be printed directly on the board 91, or they may feature on a sheet of paper that contains a hole level with the displaying means 92 and that rests on or is fastened to the board 91.

The characters 93 are significant of the location on the board 91 in which they are found in thus allow the direction of the gaze of the person looking at the reading support 9 to be known. To allow the person to look at the displaying means 92, the position of the reading support 9 may be translationally and rotatably adjusted. As indicated by the arrows (d, e, f) in FIG. 4A, the reading support 9 may especially be translated in directions (d, e) perpendicular to the direction of the gaze.

According to one preferred embodiment, the device includes means for discriminating the two eyes. These means may, for example, consist of a polarizer-analyzer pair between the corrective holder and the pattern. The displaying means 92 may, for example, comprise a polarized display, such as a liquid-crystal screen. Thus, it is possible to block the view for one of the eyes of the patient by turning a polarizer, for example placed in one of the corrective holders 3, so that its main axis is perpendicular to the polarization direction of the light waves emitted by the screen. This makes it possible to measure near- or intermediate-vision subjective refraction for each eye independently, without mechanically covering the other eye. Thus, the two eyes look at the target, but the pattern may be made out by only one eye at a time, thereby making it possible to measure acuity for only one eye at a time while remaining under the conditions of a normal lowered binocular gaze.

Alternatively, the means for discriminating between the right eye and left eye may be means conventionally employed for stereoscopic vision, such as for example anaglyphs in combination with spectacles with red and green eyeglasses, electroshutters or auto-stereoscopic screens. Directive filters such as "privacy filters" (sold, for example, by 3M) may also be considered.

According to other advantageous embodiments (not shown) of the device of the present invention, the means for determining the direction of the gaze may comprise means for acquiring and processing images. The image-acquiring means may consist, for example, of a video camera 92 placed on the reading support 9, instead of the pattern described above (see FIG. 4B). It is thus possible to determine the direction of the gaze, either by determining eye rotation center using scale markers on the corrective holders or on the chin rest, or by determining the positions of the pupils by observing light reflected from the corneas. In the second case, the means for determining gaze direction also comprise a light-emitting means emitting light in the direction of the eyes of the person, for example a light emitting diode (LED).

According to a second aspect, the present invention relates to a method for measuring the near- and/or intermediate-vision subjective refraction of a person. Advantageously, the method is implemented by means of a measuring device according to the embodiments described above. The method comprises the following steps:

In front of each eye of the person, at least one corrective lens corresponding to his far-vision prescription is placed by means of a corrective holder. The corrective holders 3 may be those described with reference to FIGS. 1 and 2A. It is thus possible to verify the far-vision visual acuity of the person. For the measurement of far-vision subjective refraction, the patient looks at a pattern displayed on a vertical plane or eye chart at about 5 to 6 m from the corrective holders 3, typically straight in front of him. The corrective holders 3 are not inclined to the vertical. The angle of convergence α between the two corrective holders is regulated to zero and the two corrective holders 3 are not tipped one relative to the other. Specifically, as seen above, in far vision, the sighting distance being about 5 m to 6 m, the angle of convergence between the axes of the eyes is close to zero.

According to the method of the invention, in front of each eye of the person, at least one corrective lens corresponding to his near- and/or intermediate-vision prescription is then placed by means of the corrective holder. According to this embodiment, for near vision, the corrective holder bears, at the end of the measurement, at least the following elements: the far-vision correction (namely, the spherical and/or cylindrical correction), the lens providing the "add" spherical correction for near vision, the lens providing the "add" cylindrical correction for near vision, and a sight.

In order to determine the direction of the gaze of the person and to guide the gaze onto the pattern, the sight is placed in front of each eye of the person by means of the corrective holder 3. The sight is preferably a cylinder 5 as described above with reference to FIG. 3A. The relative positions of the corrective holders 3 are thus adjusted in order to make the axes of the sights converge. The positions of the corrective holders 3 are adjusted in order to make, for each eye, the axis of the eye and the axis of the sight 5 coincide. Thus, when the gaze of the person is lowered in near vision, for example, the eyes of the person remain perfectly centered relative to the corrective eyeglass(es).

The near- and/or intermediate-vision visual acuity of the person is then measured. The sight may be removed to carry out this measurement.

For the measurement of near-vision subjective refraction, the patient looks at the pattern on a reading support 9 preferably placed at about 40 cm from the corrective holders 3. The reading support 9 may include a displaying means 92 as detailed with reference to FIGS. 4A and 4B. With reference to FIG. 4A, the distance between the reading support 9 and the corrective holders 3 may be adjusted by translationally moving the reading support 9 (in the direction indicated by the arrow e). Typically, the person lowers his gaze. This corresponds to the natural near-vision posture adopted by a person, for example, to read. In order for the person to look perpendicularly through the centers of the corrective eyeglasses that are intended to be placed in the corrective holders 3, the corrective holders 3 must be inclined in the same way as the eyes using the sights 5, as described above. The angle of inclination γ of the corrective holders 3 is about 0 to 45° to the vertical, and preferably about 36°. Advantageously, the reading support 9 is also inclined at an angle β to the vertical of about 0 to 45°, and preferably of about 36°. In one preferred embodiment, the plane of the reading support 9 and the plane containing the corrective holders 3 are substantially parallel in order to guarantee a good visibility of the pattern. Moreover, it is also possible to incline the headrest (7) for a more natural posture.

For the measurement of intermediate-vision subjective refraction, the patient looks at the pattern on the reading support 9 preferably placed at about 70 cm to 100 cm from the corrective holders 3. Similarly to the near-vision case, the person may lower his gaze, without moving his head. This corresponds to the natural posture that a person would adopt, for example, to carry out household tasks or to look at a computer screen. The corrective holders 3 must be inclined in the same way as the eyes using the sights 5 as described above. The angle of inclination γ for intermediate vision may be about 20° to the vertical. The reading support 9 is also inclined at an angle β to the vertical.

It is therefore necessary for the distance between the corrective holders 3 and the reading support 9 to be able to be adjusted independently of the inclinations of the corrective holders 3 and the reading support 9.

Taking into account the lowering of the gaze of the person via the inclinations and height of the reading support 9 and corrective holders 3 also allows any variation in the spherical or astigmatic refraction of the eye to be correctly evaluated. Specifically, since the eye turns slightly when lowered, the axis of the cylindrical correction is not the same for a straight-ahead gaze (into the distance) and a lowered gaze (onto a book, for example). The device and method according to the described embodiments allow the cylindrical correction required to design, for example, progressive corrective eyeglasses that are perfectly suited both to the far vision, the intermediate vision and the near vision of a wearer, to be correctly determined.

According to one preferred embodiment of the method according to the invention, the step of measuring near- and/or intermediate-vision visual acuity comprises discriminating the two eyes. According to one example, the pattern is displayed on a liquid-crystal screen, and the step of measuring visual acuity comprises the following steps. A polarizer is placed in front of each eye of the person by means of the corrective holder. The first polarizer is adjusted so that the pattern is visible to the first eye, and the second polarizer is adjusted so that the pattern is not visible to the second eye. The pattern is visible when the main axis of the polarizer coincides with the polarization direction of the light waves emitted by the screen. The pattern is not visible when the main axis of the polarizer is perpendicular to the polarization direction of the waves. Near- and/or intermediate-vision visual acuity (the mode being determined by the distance of the pattern relative to the eyes) is then measured for the first eye. This process is repeated for the second eye.

According to advantageous embodiments of the method of the invention, instead of using sights as described above, the step of determining the direction of the gaze may be carried out by determining either the eye rotation center (ERC) or the positions of the pupils of the person.

For the ERC measurement, the patient is positioned in a set way (for example, with a sighting distance of 40 cm and the gaze lowered by 36° to the horizontal). The patient looks at the center of the objective of the video camera and photos are taken with the chin rest 71 and forehead rest 73 in various positions (for example, with θ=0°, 20°, −20°, see FIG. 1). The photos taken may then be analyzed in order to calculate the positions of the ERCs relative, for example, to the chin rest 71 and to the corrective holders 3, the latter advantageously being equipped with scale markers. The corrective holders 3 may then be positioned perpendicularly to and centered on the straight lines passing through the ERCs and the center of the objective.

For the measurement of the ERCs, the photos may also be taken by a plurality of video cameras or by a single movable video camera, the patient looking at the video cameras in succession and the chin rest remaining fixed.

For the measurement of the positions of the pupils, the positions of reflections of light (emitted, for example, by an LED located on the reading support 9 and emitting in the visible or infrared spectrum) relative to the corrective holders 3 are observed, the latter being equipped with reticles marking the centers of the corrective holders 3. The patient is correctly positioned when the reflections are well centered relative to the reticles.

Preferably, the method according to the invention furthermore comprises iteratively adjusting, by means of adjusting means, the position of the corrective holders 3 in order to decrease the deviation between the position of the corrective holders 3 and a setpoint position of the corrective holders 3, the positions being relative to the pattern. As described above, the corrective holders 3 may be adjusted height wise, translationally on the horizontal plane and one relative to the other in order to adapt their separation to the pupillary distance of the patient, and indeed rotatably or pivotably. These adjustments may be manual or automated.

Therefore, and very advantageously, the determination of the direction of the gaze of the patient may thus be carried out completely automatically. For example, the adjustments to the various portions of the headrest 7 (which portions were detailed above) and those to the corrective holders 3 may be determined and controlled by a computer provided with a dedicated interface and applied using motorized adjusting means. The corrective holders 3 may then be correctly aligned and centered relative to the gaze axes of the person reliably, rapidly and efficiently.

The invention claimed is:

1. A device for measuring the near- and/or intermediate-vision subjective refraction of a person, the device comprising:
    a corrective holder configured to receive at least one corrective lens for each eye of the person;
    wherein the corrective holders are moveable relative to one another to adjust a convergence angle (α) between the axes of the lenses when the corrective lenses are disposed within the corrective holders.

2. The device of claim 1, wherein the convergence angle (α) between the axes of the lenses is adjustable between 0° and 30°.

3. The device of claim 1, further adapted to determine the direction of the gaze, so as to adjust the relative positions of the corrective holders in order to make the directions of the gaze of each eye converge with the convergence angle (α), so as to guide the gaze of the person onto a pattern during use.

4. The device of claim 3, wherein the inclination of each corrective holder is regulatable.

5. The device of claim 3, further comprising a reading support arranged at a distance and angle that may be varied relative to the corrective holders, the reading support being adapted to display the pattern during use.

6. The device of claim 3, wherein determining the direction of the gaze comprises use of, for each eye, a sight adapted to be placed in front of the eye by the corrective holder during use.

7. The device of claim 6, wherein the sight includes an entrance element and an exit element able to be aligned along the direction of the gaze between the eye and the target during use.

8. The device of claim 3, wherein determining the direction of the gaze comprises acquiring and processing images during use.

9. The device of claim 8, wherein determining the direction of the gaze further comprises an emitting light in the direction of each eye of the person during use.

10. The device of claim 1, further comprising adjusting means for decreasing the deviation between the position of the corrective holders and a setpoint position of the corrective holders, the positions being relative to the pattern, wherein the setpoint position corresponds to a position of the corrective holders in which the person looks perpendicularly through the center of the lenses.

11. The device of claim 1, further adapted to discriminate between each eye.

12. A method for measuring near- and/or intermediate-vision subjective refraction of a person with the device of claim 1, the method comprising:
   placing, in front of each eye of the person at least one corrective lens corresponding to the person's near- and/or intermediate-vision prescription, wherein the lenses are held in the corrective holders;
   varying positions of the corrective holders in order to adjust the convergence angle ($\alpha$) between the axes of the lenses; and
   determining near- and/or intermediate-vision visual acuity of the person.

13. The method of claim 12, further comprising:
   determining a direction of gaze of each eye; and
   adjusting relative positions of the corrective holders in order to make the directions of the gaze converge with the convergence angle ($\alpha$), so as to guide the gaze of the person onto a pattern.

14. The method of claim 13, wherein determining the direction of the gaze comprises placing the sight in front of each eye with the corrective holder.

15. The method of claim 13, wherein determining the direction of the gaze comprises determining eye rotation center.

16. The method of claim 13, wherein determining the direction of the gaze comprises determining positions of pupils.

17. The method of claim 12, further comprising inclining a plane containing the corrective holders in order to lower the directions of the gaze by a pantoscopic angle ($\gamma$).

18. The method of claim 13, wherein measuring near- and/or intermediate-vision visual acuity comprises:
   discriminating between each eye; and
   measuring the near- and/or intermediate-vision visual acuity for each eye independently.

19. The method of claim 12, further comprising a step of iteratively adjusting the position of the corrective holders in order to decrease deviation between the position of the corrective holders and a setpoint position of the corrective holders, the positions being relative to a pattern, wherein the setpoint position corresponds to a position of the corrective holders in which the person looks perpendicularly through centers of the lenses.

* * * * *